United States Patent [19]

Tsunemi et al.

[11] Patent Number: 5,550,282

[45] Date of Patent: Aug. 27, 1996

[54] BIFUNCTIONAL AROMATIC CYANATES, PREPOLYMERS AND ELECTRICAL LAMINATES MADE THEREFROM

[75] Inventors: Hidenari Tsunemi, Adogawacho; Toshinobu Nakata, Otsu, both of Japan

[73] Assignee: Kanegafuchi Kagaku Kogyo Kabushiki Kaisha, Osaka, Japan

[21] Appl. No.: 274,520

[22] Filed: Jul. 13, 1994

Related U.S. Application Data

[62] Division of Ser. No. 228,170, Apr. 15, 1994, Pat. No. 5,488,144, which is a division of Ser. No. 996,754, Dec. 24, 1992, abandoned.

[30] Foreign Application Priority Data

Dec. 27, 1991 [JP] Japan .................. 3-359938
Feb. 26, 1992 [JP] Japan .................. 4-75148

[51] Int. Cl.$^6$ ........................... C07C 71/00
[52] U.S. Cl. ............... 560/301; 528/422; 528/211
[58] Field of Search .............. 252/182.3; 560/301; 528/422, 211

[56] References Cited

U.S. PATENT DOCUMENTS

| | | | |
|---|---|---|---|
| 4,060,541 | 11/1977 | Sundermann | 260/453 |
| 4,094,852 | 6/1978 | Sundermann | 260/37 |
| 4,097,455 | 6/1987 | Burkhardt et al. | |
| 4,740,584 | 4/1988 | Shimp | |
| 4,745,215 | 5/1988 | Cox et al. | |
| 4,751,323 | 6/1988 | Woo et al. | |
| 4,839,442 | 6/1989 | Craig, Jr. | 528/422 |
| 4,931,545 | 6/1990 | Shimp et al. | |
| 5,068,309 | 11/1991 | Shimp et al. | 528/211 |
| 5,149,863 | 9/1992 | Shimp et al. | 560/301 |

FOREIGN PATENT DOCUMENTS

| | | |
|---|---|---|
| 2286129 | 9/1975 | France |
| 2301514 | 2/1976 | France |
| 1526450 | 9/1978 | Germany |

OTHER PUBLICATIONS

Chemical Abstracts, 114(20):187155S. 1991.
Chemical Abstracts, 79:105065; Korshak et al.; 1973.
Chemical Abstracts, vol. 79, No. 17, Oct. 29, 1973, 105605k.
H. Hoyer, Chemische Berichte, vol., 94, No. 4, 1961.

*Primary Examiner*—Samuel Barts
*Attorney, Agent, or Firm*—Millen, White, Zelano, & Branigan, P.C.

[57] ABSTRACT

Dislcosed is a curable composition of a partially trimerized prepolymer of the dicyanate ester of the formula

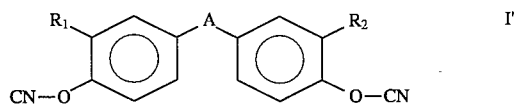

wherein $R_1$ and $R_2$ are the same or different and each is alkyl, perfluoroalkyl, aryl or halogen; and A is a bridge selected from the group consisting of a direct bond, methylene optionally mono- or disubstituted by alkyl, perfluoroalkyl and/or aryl, a five or six membered cycloalkylene, sulfonyl, thio, oxy, carbonyl, phenylene, and xylylene optionally substituted by alkyl at on or both methylene carbon atoms is useful in the manufacture of electrical laminates having excellent dielectric properties in the GHz region.

12 Claims, No Drawings

BIFUNCTIONAL AROMATIC CYANATES, PREPOLYMERS AND ELECTRICAL LAMINATES MADE THEREFROM

This application is a divisional of application Ser. No. 08/228,170, filed Apr. 15, 1994, now U.S. Pat. No. 5,488,144 which is a divisional of application Ser. No. 07/996,754, filed Dec. 24, 1992, now abandoned.

BACKGROUND OF THE INVENTION

This invention relates to novel bifunctional aromatic cyanates and prepolymers made therefrom for producing thermosetting resins having excellent dielectic properties. Such resins find use in fabricating various electric and electronic parts and electrical laminates in particular. The term "electrical laminates" as used herein refers to unclad insulation boards for mounting various parts thereon as well as metal clad laminates for use in the manufacture of printed circuit boards.

Recently the frequencies used in electronic communication equipments, computers and the like are in a high frequency region such as megahertz (MHz) or gigahertz (GHz) regions. Insulation materials used in such high frequency regions must have a low dielectric constant as well as a low dielectric loss tangent in such high frequency regions. To achieve this a variety of low dielectric constant and dielectric loss tangent resins have been developed. Cyanate ester resins are excellent among others in these dielectric properties. Bisphenol A dicyanate ester resins, for example, have been used in fabricating electrical laminates. Japanese Laid Open Patent Application No. 250359/1988 discloses a fluorine-containing dicyanate ester for producing thermosetting resins having excellent dielectric properties.

The prior art dicyanate ester resins including the afore mentioned resins have excellent dielectric properties compared to epoxy, polyester, phenol and polyimide resins which are conventionally used in the manufacture of electrical laminates. They are, however, not fully satisfactory with respect to dielectric loss tangent in the high frequency regions and in the GHz region in particular. It is desirable for electrical laminates used in the telecommunication field to have a dielectric loss tangent less than 0.005. It is also desirable for the matrix resin of such laminates to have a dielectric loss tangent of less than 0.006, preferably less than 0.005, and more preferably less than 0.004 in the GHz region. For computer application, the matrix resin of electrical laminates should desirably have a dielectric constant of less than 3.0, more desirably less than 2.8, and most desirably less than 2.7 in the GHz region for enabling faster operation.

A need exists, therefore, for a thermosetting resin having excellent dielectric properties and dielectric loss tangent in particular in the UHF region and the GHz region particularly.

SUMMARY OF THE INVENTION

The above and other requirements may be met by a novel dicyanate ester of the formula:

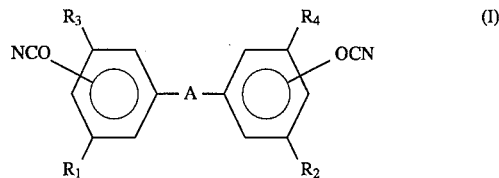

wherein $R_1$, $R_2$, $R_3$ and $R_4$ are the same or different and each is hydrogen, alkyl, perfluoroalkyl, aryl or halogen; A is a bridge selected from the group consisting of direct bond, methylene optionally mono- or di-substituted by alkyl, perfluoroalkyl and/or aryl, a five or six membered cycloalkylene, sulfonyl, thio, oxy, carbonyl, phenylene, and xylylene optionally substituted by alkyl at one or both methylene carbon atoms; with the proviso that when the cyanato group is at the para-position relative to the bridge A, $R_1$ and $R_2$ cannot mean hydrogen simultaneously.

In another aspect, the present invention provides a prepolymer produced by cyclization-trimerizing the dicyanate ester of the formula I to a cyanate group-conversion rate less than 50%.

In a further aspect, the present invention provides an electrical laminate produced by laminating a plurality of fibrous substrates impregnated with the dicyanate ester of formula I or its prepolymer followed by curing the laminate into a rigid state.

The cyanate ester and prepolymer of the present invention find other electrical and electronic applications as adhesive, coating, casting and other resin compositions where a low dielectric loss tangent and thus a low transmission loss in a high frequency region and in the GHz region in particular are desired.

DETAILED DESCRIPTION OF THE INVENTION

The preferred dicyanates of formula I are those wherein $R_1$ and $R_2$ are both $C_1$–$C_4$ alkyl, aryl or halogen; $R_3$ and $R_4$ are both hydrogen, $C_1$–$C_4$ alkyl or halogen; and A is methylene, 2,2-propylene, oxy or 1,1-cyclohexylene, e.g., 2,2-bis(4-cyanato-3-isopropylphenyl)propane, 2,2-bis(4-cyanato-3-sec.-butylphenyl)propane, 2,2-bis(4-cyanato-3-methylphenyl)propane, 2,2-bis(4-cyanato-3-phenylphenyl)propane, 2,2-bis(4-cyanato-3-fluorophenyl)propane, bis(4-cyanato-3-methylphenyl)methane, 1,1-bis(4-cyanato-3-phenylphenyl)cyclohexane, 4,4'-dicyanato-3,3'-dimethyldiphenyl ether, bis(2-cyanato-5-methyl)methane, bis(2-cyanato-3,5-dimethylphenyl)methane, or bis(2-cyanato-5-t-butyl)methane.

The dicyanate ester of the formula I may be synthesized, as is well-known, by reacting cyanogen halide with the corresponding polyphenol of the formula:

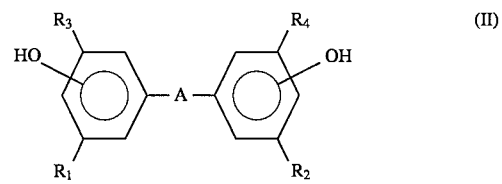

wherein all symbols are as defined above.

$R_1$, $R_2$, $R_3$ and $R_4$ are the same or different and each is hydrogen, alkyl, perfluoroalkyl, aryl or halogen. A $C_1$–$C_5$ alkyl such as methyl, ethyl, n-propyl, isopropyl, n-butyl, isobutyl, t-butyl, or isomeric pentyl may be mentioned. Methyl, ethyl, isopropyl and t-butyl are particularly preferable. As perfluoroalkyl, a $C_1$–$C_4$ perfluoroalkyl such as perfluoromethyl or perfluoroethyl is preferable. Examples of aryl include phenyl, a $C_1$–$C_4$ alkyl-mono- or disubstituted phenyl such as o-, m- or p-tolyl, 1- or 2-naphthyl, a $C_1$–$C_4$ alkyl-monosubstituted naphthyl. Phenyl and a $C_1$–$C_4$ alkyl-monosubstituted phenyl are particularly preferable. Halogens include fluorine, chlorine, bromine and iodine. Chlorine and bromine are preferable.

The bridge A may be a direct bond, methylene or mono- or di-substituted methylene with alkyl, perfluoroalkyl and/or aryl such as 1,1-ethylidene, 1,1-propylidene, 2,2-propylidene, 3,3-pentylidene, mono- or diphenylmethylene, methylphenylmethylene, ethylphenylmethylene, 2,2-perfluoropropylidene and the like. The bridge A may also be a five or six membered cycloalkylene such as cyclopentylene or cyclohexylene, sulfonyl namely —$SO_2$—, thio namely —S—, oxy namely —O—, carbonyl namely —CO—, or xylylene optionally substituted by a $C_1$–$C_2$ alkyl at one or both methylene carbon atoms. The term "xylylene" refers to 1,2-, 1,3 or 1,4-benzene-bismethylene bridge. Tetramethylxylylene is a typical example of methylene-alkylated xylylenes.

The starting polyphenol of the formula II may be reacted with a cyanogen halide in the presence of an acid acceptor to produce the corresponding dicyanate ester of formula I. The reaction is known per se as is disclosed, for example, in U.S. Pat. No. 3,553,244 whose entire disclosure is incorporated herein by reference. For example, to a stoichiometric mixture of the polyphenol and cyanogen bromide in acetone is added dropwise an amount of triethylamine at a temperature between 0° C. and 10° C. with stirring. After removing the resulting triethylamine hydrobromide, the dicyanate ester may be isolated from the reaction mixture by any conventional method.

A particularly preferred class of the dicyanate esters of the formula I include those wherein $R_1$ and $R_2$ are the same and each is a $C_1$–$C_4$ alkyl, phenyl, tolyl, a $C_1$–$C_4$ perfluoroalkyl or halogen; $R_3$ and $R_4$ are the same and each is hydrogen or a $C_1$–$C_4$ alkyl; and A is methylene, 2,2-propylidene, oxy or 1,1-cyclohexylene. Specific examples thereof include 2,2-bis(4-cyanato-3-methylphenyl)propane, 2,2-bis(4-cyanato-3-isopropylphenyl)propane, 2,2-bis(4-cyanato-3-sec.-butylphenyl)propane, 2,2-bis(4-cyanato-3-phenylphenyl)propane, 2,2-bis(4-cyanato-3-fluorophenyl)propane, bis(4-cyanato-3-methylphenyl)methane, 1,1-bis(4-cyanato-3-phenylphenyl)cyclohexane, 4,4'-dicyanato-3,3'-dimethyldiphenyl ether, bis(2-cyanato-5-methylphenyl)methane there bis(2-cyanato-3,5-dimethylphenyl)methane and the like.

The dicyanate ester of the formula I trimerizes into a triazine structure upon heating at an elevated temperature. The prepolymer of the present invention may be produced by heating the dicyanate ester of formula I at a temperature and for a length of time sufficient to effect less than 50%, preferably from 10 to 40% conversion of the cyanato groups into the triazine structure. Generally this requires heating at a temperature between 150° C. and 200° C. for a length of time between 1 and 10 hours.

The dicyanate esters and prepolymers of the present invention may be used in the manufacture of electrical laminates and other electrical and electronic parts as matrix resin or as casting, adhesive or coating composition. For use the dicyanate ester and prepolymer may be intermixed, or blended with a conventional thermosetting resin such as epoxy, polyester, epoxy-acrylate, urethane-acrylate, diallyl phthalate, spiropyrane, phenol, polyimide or like resins, or a conventional thermoplastic resin such as fluororesin, polyphenyleneoxide, polyphenylenesulfide or like resins.

For casting purpose, the dicyanate ester or prepolymer in a molten state is cast into a mold and allowed to cure at an elevated temperature. The casting composition may optionally contain a small amount of a curing catalyst such as imidazole compounds, tertiary amines or organometallic compounds. Organometallic compounds such as cobalt octanate, zinc octanate, cobalt naphthenate or zinc naphthenate are preferable. The curing reaction may be accelerated by the addition of a small amount of phenol such as bisphenol A, bisphenol F, bisphenol S or p-nonylphenol.

Electrical laminates may be produced by any conventional method using prepregs impregnated with the dicyanate esters and prepolymers of the present invention. Examples of substrates used in the preparation of prepregs include glass fiber substrates such as glass cloth or glass nonwoven fabric, cellulosic substrates such as kraft paper or cotton linter paper, synthetic fiber fabric such as aramide cloth or aramide nonwoven fabric. Composite laminates may be produced using different type substrates in combination. The dicyanate esters and prepolymers are made up to a varnish by dissolving in a volatile organic solvent. Examples of solvents include ketones such as acetone, methyl ethyl ketone or methyl isobutyl ketone; aromatic hydrocarbons such as toluene or xylene; ethers such as dioxane, tetrahydrofuran or ethylene glycol monomethyl ether; alcohols such as methanol, ethanol or isopropyl alcohol; amides such as dimethylformamide or dimethylacetamide; and mixtures of these solvents. Aromatic hydrocarbons and ketones such as acetone or methyl ethyl ketone are suitable. The varnish may contain a catalyst and/or phenol as described above as well as fillers such as alumina, aluminum hydroxide, antimony tri- or pentoxide, zinc oxide, titanium dioxide, silica powder, quartz powder, glass powder, ceramic microballoons, or mixtures thereof. After impregnating with the varnish, the substrate may be dried under heating to remove the solvent and also to semicure the resin. Alternatively, the prepreg may be produced by impregnating the substrate with a molten liquid of the dicyanate ester or prepolymer.

The production of electrical laminates may be batchwise or continuous. In the batchwise process, a plurality of prepregs of a predetermined size are stacked with a cladding metal foil being placed on one or both sides, and compressed between a pair of hot plates of a press under heat and pressure. In the continuous precess, a continuous length of prepreg rolled in a coil is prepared. A plurality of prepregs are paid down from their coils, led into a continuous press such as double belt press along with the cladding metal foil, and then compressed in the press under heat and pressure. Alternatively the laminate may be produced continuously by laying down a plurality of substrates, impregnating the plurality of substrates with a molten liquid of the dicyanate ester or prepolymer, joining the impregnated substrates into a laminate, applying a cladding metal foil on one or both side, and then curing the laminate without applying pressure.

For use as adhesive or coating compositions, the above prepolymer varnish or molten liquid optionally containing various additives as described above may be employed as such.

The following examples are intended to further illustrate the invention without limiting thereto. All parts and percents therein are by weight unless otherwise indicated.

EXAMPLE 1

A three necked flask equipped with a drip funnel, thermometer and stirrer was charged with a solution of 44.5 g of cyanogen bromide and 62.5 g of 2,2-bis(4-hydroxy-3-isopropylphenyl)propane in 300 ml of acetone. The inner temperature was kept at a temperature of between −5° C. and +3° C. The starting polyphenol was produced by condensing o-isopropylphenol and acetone in the presence of an acid catalyst followed by purification. To the solution was added dropwise 41.5 g of triethylamine at a rate sufficient to maintain the inner temperature below 10° C. After the addition, the reaction mixture was stirred for additional 2 hours at a temperature below 10° C. and then filtered to remove white crystals of triethylamine hydrobromide. The filtrate was poured in a large volume of water whereupon a pale yellow oil was separated. This oil was extracted with methylene chloride, washed with water and purified by column chromatography. A colorless transparent oil was obtained at a yield of 60% of theory. The product was identified as 2,2-bis(4-cyanato-3-isopropylphenyl)propane by the IR and NMR spectra thereof. The assignments of cyanato group in the IR spectrum was at 2260 $cm^{-1}$.

EXAMPLE 2

Analogous to Example 1, 2,2-bis(4-cyanato-3-sec.butylphenyl)propane was synthesized from 68.1 g 2,2-bis(4-hydroxy-3-sec.butylphenyl)propane as white crystals melting at 78° C. at a yield of 50% of theory. The product was identified by the NMR spectrum thereof as well as the absorption of cyanato group at 2260 $cm^{-1}$ and the absence of phenolic hydroxyl in the IR spectrum thereof.

EXAMPLE 3

Analogous to Example 1, 2,2-bis(4-cyanato-3-methylphenyl)propane was synthesized from 51.3 g of 2,2-bis(4-hydroxy-3-methylphenyl)propane. 58.1 g of the product was obtained as white cryastals melting at 71° C. In this example, the solvent used was 400 ml of isopropyl alcohol and the product was isolated by simply filtering the reaction mixture followed by washing with water. The product was identified by the NMR spectrum thereof as well as the absorption of cyanato group at 2276 $cm^{-1}$ and 2251 $cm^{-1}$, and the absence of phenolic hydroxyl in the IR spectrum thereof.

EXAMPLE 4

Analogous to Example 1, 76.1 g of 2, 2-bis(4-hydroxy-3-phenylphenyl)propane was reacted with a stoichiometric amount of cyanogen bromide with the addition of triethylamine in 300 ml of tetrahydrofuran. After the reaction, the mixture was poured in a large volume of water whereupon white crystals were separated. Recrystallization gave 53.1 g of the product propane, 2,2-bis(4-cyanato-3-phenylphenyl) as white crystals which were then identified by the NMR and IR spectra thereof.

EXAMPLE 5

Analogous to Example 3, 2,2-bis(4-cyanato-3-fluorophenyl)propane was synthesized from 52.9 g of 2,2-bis(4-hydroxy-3-fluorophenyl)propane. 45.2 g of the product was obtained as white crystals melting at 52° C. which were then identified by the NMR and IR spectra thereof.

EXAMPLE 6

Analogous to Example 3, bis(4-hydroxy-3-methylphenyl)methane was synthesized from 45.7 g of bis(4-cyanato-3-methylphenyl)methane. 38.2 g of the product was obtained as white crystals melting at 111°–112 ° C. which were then identified by the NMR and IR spectra thereof.

EXAMPLE 7

Analogous to Example 1, 1,1-bis(4-cyanato-3-phenylphenyl)cyclohexane was synthesized from 84.1 g of 1,1-bis(4-hydroxy-3-phenylphenyl)cyclohexane. 300 ml of tetrahydrofuran was used in the reaction as a solvent. Column chromatography of a pale yellow oil of the crude product gave 28.3 g of white crystals which were then identified by the IR and NMR spectra thereof.

EXAMPLE 8

Analogous to Example 3, 4,4'-dicyanato-3,3'dimethyldiphenyl ether was synthesized from 46.0 g of 4,4'-dihydroxy-3,3'-dimethyldiphenyl ether. 43.5 g of the product was obtained as white crystals which were then identified by the IR and NMR spectra thereof.

EXAMPLE 9

A three necked flask equipped with a drip funnel, thermometer and stirrer was charged with a solution of 46.6 g of bis(2-hydroxy-5-methylphenyl)methane and 46.6 g of cyanogen bromide in 150 ml of isopropyl alcohol. The starting polyphenol was produced by condensing p-cresol with formaldehyde in the presence of an acid catalyst followed by purification. The inner temperature was kept at a temperature between −5° C. and +3° C. To the solution was added dropwise 41.5 g of triethylamine at a rate sufficient to maintain the inner temperature below 10° C. After the addition, the reaction mixture was stirred for additional 2 hours at a temperature below 10° C. The resulting white precipitates were recovered by filtration and then washed with water thoroughly whereupon 36 g of white crystals melting at 109°–110° C. were obtained. The product was identified as bis(2-cyanato-5-methylphenyl)methane in the IR and NMR spectrometry thereof. The assignment of cyanato group in the IR spectrum was at 2242 $cm^{-1}$ and 2272 $cm^{-}$.

EXAMPLE 10

Analogous to Example 9, bis(2-cyanato-3,5-dimethylphenyl)methane was synthesized by reacting bis(2-hydroxy-3, 5-dimethylphenyl)methane and cyanogen bromide. The product was identified by the elementary analysis and IR spectrum thereof. The assignment of cyanato group was at 2240 $cm^{-1}$ and 2271 $cm^{-1}$.

EXAMPLE 11

Analogous to Example 9, bis(2-cyanato-5-t-butylphenyl) methane was synthesized by reacting bis(2-hydroxy-5-t-butylphenyl)methane and cyanogen bromide. The product was identified by the elementary analysis and IR spectrum thereof. The assignment of cyanato group was at 2241 $cm^{-1}$ and 2273 $cm^{-1}$.

Comparative Example 1

Analogous to Example 3, 2,2-bis(4-cyanatophenyl)propane was synthesized by reacting bisphenol A with cyanogen bromide.

Comparative Example 2

Analogous to Example 3, bis(4-cyanatophenyl)methane was synthesized by reacting bisphenol F with cyanogen bromide.

Comparative Example 3

Analogous to Example 3, 4,4'-dicyanotodiphenyl ether was synthesized by reacting 4,4'-dihydroxydiphenyl ether with cyanogen bromide.

Comparative Example 4

Analogous to Example 3, 2,2-bis(4-cyanatophenyl) perfluoropropane was synthesized by reacting 2,2-bis(4-hydroxyphenyl)perfluoropropane and cyanogen bromide.

Evaluation of Dielectric Properties

The dicyanate esters produced in Examples 1–11 and Comparative Examples 1–4 were heated at a temperature between 150° C. and 200° C. for a period from 1 to 10 hours to achieve 10–40% conversion of cyanato group into the triazine structure. The resulting prepolymers were cast into a Teflon mold and cured at 200° C. for 1–5 hours and then at 250° C. for 3 hours to produce a specimen having 5 mm thickness. Using this test specimen, dielectric properties in the GHz frequency region were determined. Measurements of dielectric constant and dielectric loss tangent were made by the perturbation principle using a network analyzer (Model HP8410B) and a rectangular cavity resonator having a resonant frequency of about 2.5 GHz sold by SHIMADA RIKA K.K. The results are shown in Table 1.

TABLE 1

Dielectric Properties of Resins

| Dicyanate | Dielectric Constant (2.5 GHz) | Dielectric Loss Tangent (2.5 GHz) |
|---|---|---|
| Example 1 | 2.57 | 0.0029 |
| Example 2 | 2.56 | 0.0031 |
| Example 3 | 2.75 | 0.0035 |
| Example 4 | 2.69 | 0.0041 |
| Example 5 | 2.75 | 0.0056 |
| Example 6 | 2.81 | 0.0032 |
| Example 7 | 2.80 | 0.0055 |
| Example 8 | 2.86 | 0.0030 |
| Example 9 | 2.78 | 0.0019 |
| Example 10 | 2.70 | 0.0020 |
| Example 11 | 2.68 | 0.0019 |
| Comp. Ex. 1 | 2.84 | 0.0069 |
| Comp. Ex. 2 | 2.91 | 0.0066 |
| Comp. Ex. 3 | 2.95 | 0.0063 |
| Comp. Ex. 4 | 2.65 | 0.0060 |

From Table 1, it is apparent that the resins produced from the dicyanate esters of the present invention are excellent in dielectric loss tangent compared to the prior art resins.

EXAMPLE 12

2,2-bis(4-cyanato-3-isopropylphenyl)propane produced in Example 1 was heated in a flask with stirring at 150° C. for about 4 hours under the blanket of nitrogen gas until 35–40% conversion of cyanato groups into the trazine structure was achieved.

A varnish was prepared by dissolving 100 parts of the resulting prepolymer in 40 parts of methyl ethyl ketone containing 0.05 parts of zinc octanate with gentle stirring and warming. The viscosity of this varnish was 1.5 poise at 20° C.

A 7628 type E glass cloth (WEA18W sold by NITTO BOSEKI CO., LTD.) was impregnated with the varnish, dried at 100° C. for 5 minutes and heated at 150° C. for 10 minutes. Seven sheets of the resulting prepreg were stacked with an electrolytic copper foil having 18 micron thickness being placed on both sides and molded in a press for 2 hours under a molding pressure of 20 kg/cm$^2$ at 180° C. A both sided copper clad laminate of 1.6 mm thickness was produced. A test specimen was prepared by subjecting the laminate to post curing for 2 hours at 220° and then removing cladding foil by etching.

EXAMPLES 13–22 AND COMPARATIVE EXAMPLES 5–8

Analogous to Example 12, similar laminates and specimens were produced from the dicyanate esters of Examples 2–11 and Comparative Examples 1–4.

Comparative Example 9

A test specimen was prepared by removing cladding foil from a commercially available both sided copper clad laminate of FR-4 type having 1.6 mm thickness.

Evaluation of Dielectric Properties

Specimens of the laminates of Examples 12–22 and Comparative Examples 5–9 were tested for dielectric properties by the same method as before. The results are shown in Table 2.

TABLE 2

Dielectric Properties of Laminates

| Laminate | Dielectric Constant (2.5 GHz) | Dielectric Loss Tangent (2.5 GHz) |
|---|---|---|
| Example 12 | 3.7 | 0.0033 |
| Example 12 | 3.7 | 0.0033 |
| Example 13 | 3.7 | 0.0035 |
| Example 14 | 3.9 | 0.0038 |
| Example 15 | 3.8 | 0.0042 |
| Example 16 | 3.9 | 0.0046 |
| Example 17 | 4.0 | 0.0035 |
| Example 18 | 4.0 | 0.0045 |
| Example 19 | 4.1 | 0.0036 |
| Example 20 | 3.9 | 0.0028 |
| Example 21 | 3.8 | 0.0029 |
| Example 22 | 3.8 | 0.0029 |
| Comp. Ex. 5 | 4.1 | 0.0065 |
| Comp. Ex. 6 | 4.2 | 0.0066 |
| Comp. Ex. 7 | 4.2 | 0.0063 |
| Comp. Ex. 8 | 3.8 | 0.0062 |
| Comp. Ex. 9 | 4.5 | 0.0155 |

From Table 2, it is apparent that the laminates of the present invention are excellent with respect to dielectric loss tangent compared to the prior art laminates.

We claim:

1. A curable composition comprising a partially trimerized prepolymer of a dicyanate ester of the formula:

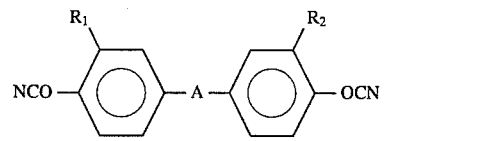

wherein R$_1$, and R$_2$ are the same or different and each is alkyl, perfluoroalkyl, aryl or halogen; and A is a bridge selected from the group consisting of a direct bond, methylene optionally mono- or disubstituted by alkyl, perfluoroalkyl and/or aryl, a five or six membered cycloalkylene, sulfonyl, thio, oxy, carbonyl, phenylene, and xylylene optionally substituted by alkyl at one or both methylene carbon atoms.

2. The curable composition of claim 1, wherein $R_1$ and $R_2$ are both $C_1$–$C_4$ alkyl, phenyl or halogen, and A is methylene, 2,2-propylene, oxy or 1,1-cyclohexylene.

3. The curable composition of claim 1, wherein said dicyanate ester is 2,2-bis(4-cyanato-3-alkylphenyl)propane, 2,2-bis(4-cyanato-3-halophenyl)propane, bis(4-cyanato-3-alkylphenyl)methane, 1,1-bis(4-cyanato-3-phenylphenyl) cyclohexane or 4,4'-dicyanate-3,3'-dialkyldiphenyl ether.

4. The curable composition of claim 1, wherein less than 50% of cyanato groups of said dicyanate ester are trimerized.

5. The curable composition of claim 1, wherein less than 50% of cyanato groups of said dicyanate ester are trimerized.

6. The curable composition of claim 1, wherein 10 to 40% of said cyanato groups are trimerized.

7. The curable composition of claim 3, wherein less than 50% of cyanato groups of said dicyanate ester are trimerized.

8. The curable composition of claim 2, wherein 10 to 40% of said cyanato groups are trimerized.

9. The curable composition of claim 3, wherein 10 to 40% of said cyanato groups are trimerized.

10. The curable composition of claim 1, which is prepared by heating the dicyanate ester of formula I at a temperature and for a length of time sufficient to effect less than 50% conversion of the cyanato groups into the triazine structure.

11. The curable composition of claim 10, wherein the conversion is from 10 to 40%.

12. The curable composition of claim 10, wherein the temperature is between 150° C. and 200° C. and the time is between 1 and 10 hours.

* * * * *